United States Patent
Marrapode et al.

(10) Patent No.: US 11,344,433 B2
(45) Date of Patent: May 31, 2022

(54) SPINAL IMPLANT SYSTEM AND METHOD

(71) Applicant: Warsaw Orthopedic, Inc., Warsaw, IN (US)

(72) Inventors: Matthew T. Marrapode, Boulder, CO (US); Larry Thomas McBride, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 4 days.

(21) Appl. No.: 16/274,574

(22) Filed: Feb. 13, 2019

(65) Prior Publication Data

US 2020/0253745 A1 Aug. 13, 2020

(51) Int. Cl.
| | | |
|---|---|---|
| *A61F 2/46* | (2006.01) | |
| *A61F 2/44* | (2006.01) | |
| *A61F 2/30* | (2006.01) | |
| *A61F 2/28* | (2006.01) | |

(52) U.S. Cl.
CPC .............. *A61F 2/4611* (2013.01); *A61F 2/28* (2013.01); *A61F 2/442* (2013.01); *A61F 2/4455* (2013.01); *A61F 2/30771* (2013.01); *A61F 2002/2835* (2013.01); *A61F 2220/0025* (2013.01)

(58) Field of Classification Search
CPC .............. A61F 2/441; A61F 2002/4415; A61F 2/4455; A61F 2/446; A61F 2002/4495
See application file for complete search history.

(56) References Cited

U.S. PATENT DOCUMENTS

| | | | |
|---|---|---|---|
| 5,549,679 A | * | 8/1996 | Kuslich .................. A61F 2/4611 623/17.12 |
| 5,741,261 A | | 4/1998 | Moskovitz et al. |
| 6,500,206 B1 | | 12/2002 | Bryan |
| 6,730,095 B2 | | 5/2004 | Olson, Jr. et al. |
| 7,651,496 B2 | | 1/2010 | Keegan et al. |
| 7,780,709 B2 | | 8/2010 | Bruneau et al. |
| 7,789,898 B2 | | 9/2010 | Peterman |
| 2003/0040800 A1 | * | 2/2003 | Li ........................... A61F 2/442 623/17.12 |
| 2004/0249471 A1 | | 12/2004 | Bindseil et al. |
| 2005/0131267 A1 | * | 6/2005 | Talmadge ............. A61M 25/10 600/3 |
| 2007/0168042 A1 | * | 7/2007 | Hudgins ................. A61F 2/441 623/17.16 |
| 2007/0173940 A1 | * | 7/2007 | Hestad ................... A61F 2/4465 623/17.12 |
| 2007/0191840 A1 | * | 8/2007 | Pond ................... A61B 17/7037 623/17.16 |
| 2008/0161929 A1 | * | 7/2008 | McCormack ...... A61B 17/7064 623/17.16 |
| 2009/0112323 A1 | * | 4/2009 | Hestad ................... A61F 2/4611 623/17.12 |
| 2010/0042219 A1 | * | 2/2010 | Antonacci ............... A61F 2/441 623/17.16 |

(Continued)

*Primary Examiner* — Matthew J Lawson
(74) *Attorney, Agent, or Firm* — Sorell, Lenna & Schmidt, LLP

(57) ABSTRACT

A spinal implant includes a body having an inner surface and a connecting wall. The inner surface defines at least one cavity and the connecting wall is disposed about the at least one cavity. The connecting wall defines at least one opening. An agent is disposable with the at least one cavity. Spinal constructs, surgical instruments, systems and methods are disclosed.

16 Claims, 7 Drawing Sheets

(56) References Cited

U.S. PATENT DOCUMENTS

| | | | |
|---|---|---|---|
| 2010/0256766 A1* | 10/2010 | Hibri | A61F 2/442 623/17.16 |
| 2011/0054408 A1 | 3/2011 | Wei et al. | |
| 2013/0110239 A1 | 5/2013 | Siegal et al. | |
| 2013/0280303 A1 | 10/2013 | Drapeau et al. | |
| 2013/0304212 A1* | 11/2013 | VonGunten | A61F 2/4611 623/17.16 |
| 2014/0277466 A1* | 9/2014 | Teisen | A61F 2/441 623/17.12 |
| 2016/0120653 A1* | 5/2016 | Hibri | A61F 2/442 29/525.01 |
| 2017/0360570 A1* | 12/2017 | Berndt | A61B 17/8685 |

* cited by examiner

– 1 –

SPINAL IMPLANT SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, lam inotomy, foraminotomy, facetectomy and implantable prosthetics. As part of these surgical treatments, spinal constructs including implants, such as, for example, bone graft, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these technologies.

SUMMARY

In one embodiment, a spinal implant is provided. The spinal implant includes a body having an inner surface and a connecting wall. The inner surface defines at least one cavity and the connecting wall is disposed about the at least one cavity. The connecting wall defines at least one opening. An agent is disposable with the at least one cavity. In some embodiments, spinal constructs, surgical instruments, systems and methods are disclosed.

In one embodiment, a spinal implant system is provided. The spinal implant system includes a polymer mesh body having an inner surface that defines a plurality of cavities. The body further includes a plurality of boundaries disposed about the cavities. The boundaries include at least one opening. At least one bone fastener is disposable with the at least one opening. An agent is disposable with the cavities.

In one embodiment, a method for treating a spine is provided. The method comprises the steps of: selecting an implant body for disposal with spinal tissue, the implant body including a first layer and a second layer that are connectable to define at least one cavity of the implant body; disposing an agent with the implant body; intra-operatively connecting the layers to form a boundary of the implant body and define the at least one cavity for disposal of the agent; and connecting the implant body with the tissue.

BRIEF DESCRIPTION OF THE DRAWINGS

The present disclosure will become more readily apparent from the specific description accompanied by the following drawings, in which.

DETAILED DESCRIPTION

Figure 1:
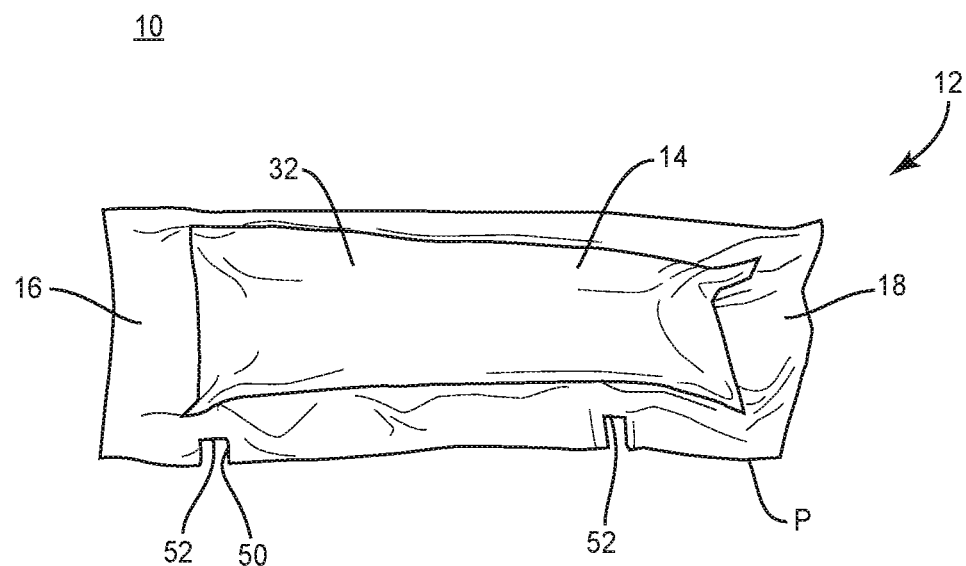
FIG. 1 is a plan view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and a method for treating a spine. In some embodiments, the present surgical system comprises one or more spinal implants employed with a spinal joint and fusion, for example, with a cervical, thoracic, lumbar and/or sacral region of a spine. In some embodiments, the surgical system and methods of the present disclosure are employed with decompression, discectomy, laminectomy, laminoplasty, fusion, fixation and implantable prosthetic procedures. In some embodiments, the present surgical system and method may be employed for a postero-lateral fusion using minimally invasive and percutaneous techniques.

In some embodiments, the present surgical system includes a spinal implant, such as, for example, a receptacle or bag configured for disposal of one or more agents, which may include bone graft and biologics. In some embodiments, the surgical system includes one or a plurality of single use fillable bags of varying geometries, features and porosities for more accurate and secure placement of bone graft and/or biologics in a lateral gutter, and/or around screw heads and laminar fusions during posterior fixation procedures. In some embodiments, the surgical system includes a series of bags with varying geometries, features and mesh types that can contain bone graft/biologics products for use in posterior fixation procedures. In some embodiments, the bags allow for more accurate and secure placement of graft in a lateral gutter and around a screw head and laminar fusions. In some embodiments, the bags are placed using screw trajectories, and the screw heads, as they are tightened, clamp the graft down and hold it in place for fusion. In some embodiments, the surgical system includes a spinal implant body that allows more accurate and secure placement of bone graft and/or biologics for posterior fixation surgeries using existing navigation and fixation technologies.

In some embodiments, the present surgical system includes a spinal implant body that provides an accurate placement and securement of bone graft in a lateral gutter and/or around screw heads, for example, with laminar fusions in posterior fixation procedures. In some embodiments, the surgical system can be used with various biologics, including synthetic and allograft offerings, in combination with open, mini-open, and percutaneous screw systems. In some embodiments, the surgical system includes a spinal implant having biologics/bone graft used to fill bags that could be provided in various configurations or sealed or shut intra-operatively. In some embodiments, the surgical system includes a spinal implant having bags with holes and slots with varying locations and geometries.

In some embodiments, the present surgical system is employed with a method comprising the steps of employing C-arm fluoroscopy and identifying screw trajectory, making an incision and inserting a PAK needle. In some embodiments, the method includes the step of inserting a guidewire and removing the PAK needle. In some embodiments, the method includes the step of placing guidewires. In some embodiments, the method includes the step of decorticating a fusion bed. In some embodiments, the method includes the step of choosing a bone graft bag with desired geometry and features, inserting bone graft into the bag, and sealing the bag. In some embodiments, the method includes the step of inserting a bone graft bag with tissue. In some embodiments, the method includes the step of pulling the bag through tissue with an inserter and placing retaining geometry of the bag around the guidewire. In some embodiments, the method includes the step of removing the inserter and placing the screws with the bag and tissue.

In some embodiments, the present surgical system is used with a method comprising the steps of employing surgical navigation and creating an incision. In some embodiments, the method includes the step of decorticating a fusion bed. In some embodiments, the method includes the step of selecting a bone graft bag with desired geometry and features, inserting bone graft into the bag, and sealing the bag. In some embodiments, the method includes the step of disposing the bag with a surgical site using surgical navigation. In some embodiments, the method includes the step of delivering the bag to the surgical site using a surgical navigation inserter. In some embodiments, the method includes the step of delivering the pedicle screws through the bag at the surgical site using a surgical navigation driver.

In some embodiments, one or all of the components of the surgical system are disposable, peel-pack, pre-packed sterile devices that can be used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise, or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
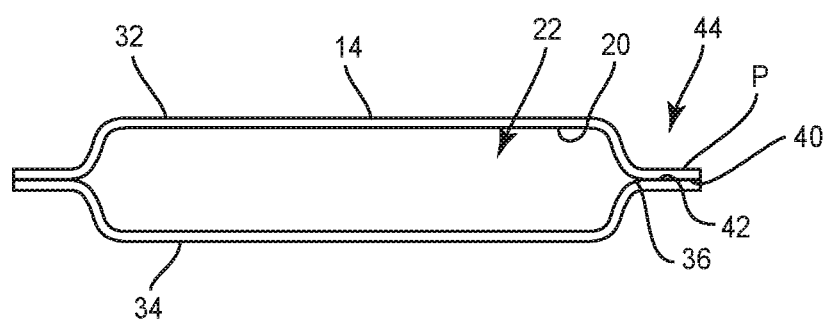
FIG. 2 is a cross section view of components of the system shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1 and 2, there are illustrated components of a surgical system 10 including a spinal implant 12.

The components of surgical system 10 can be fabricated from biologically acceptable materials suitable for medical applications, including synthetic polymers, ceramics, metals and/or their composites. For example, the components of surgical system 10, individually or collectively, can be fabricated from materials such as a polymer mesh. In some embodiments, spinal implant 12 includes a polymer mesh covering. In some embodiments, the components of surgical system 10 may be fabricated from materials, such as, for example, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), calcium sulfate, or other resorbable polymers such as polyaetide, polyglycolide, polytyrosine carbonate, polycaroplaetohe and their combinations, ceramics and composites thereof such as calcium phosphate (e.g., SKELITE™), stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®).

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including spinal implant 12 can be employed, for example, with percutaneous surgical implantation, minimally invasive surgery, mini-open and open surgical techniques to prepare a surgical site including tissue in connection with a surgical procedure, introduction of surgical instrumentation and/or delivery and introduction of one or more biomaterials and/or a spinal implant, such as, for example, receptacles, bags, pouches, one or more agents, fasteners, connectors, plates, an intervertebral implant, interbody devices and/or arthroplasty devices at a surgical site within a body of a patient, for example, a section of a spine. In some embodiments, surgical system 10 may be employed with surgical procedures, such as, for example, decompression, corpectomy and discectomy, which can include fusion and/or fixation treatments that employ spinal implants.

In some embodiments, spinal implant 12 is configured to facilitate an accurate placement and securement of an agent, for example, bone graft in a lateral gutter and around screw heads in posterior fixation procedures. In some embodiments, spinal implant system 10 includes a kit of one or a plurality of single use fillable spinal implants 12 having various features, such as, for example, geometry, porosity and/or size. Spinal implant 12 is selected for disposal with vertebrae, as described herein. A selected spinal implant 12 is disposable with vertebrae and the features of spinal implant 12 may be selected pre-operatively and/or intra-operatively such that one or more of the components of spinal implant 12 can be connected and/or assembled pre-operatively and/or intra-operatively.

Spinal implant 12 includes a receptacle configured for disposal of one or more agents, as described herein. The receptacle includes a body 14 that extends between an end 16 and an end 18. Body 14 comprises an overall rectangular configuration and a substantially rectangular cross-section with arcuate edges to a connecting wall, as described herein. In some embodiments, the overall geometry and/or cross-section of body 14 may have alternate configurations, such as, for example, oval, cylindrical, triangular, square, polygonal, irregular, uniform, non-uniform, offset, staggered, undulating, arcuate, variable and/or tapered.

Body 14 is fabricated from a flexible and/or elastic material. In some embodiments, body 14 may have flexible and/or elastic properties, such as the flexible and/or elastic properties corresponding to the material examples described above, such that body 14 provides a selective amount of flexibility, deformability, malleability and/or moldability with one or more components of surgical system 10 and/or the structural anatomy of tissue, as described herein. In some embodiments, body 14 can be flexible, elastic, semi-rigid or rigid. In some embodiments, body 14 can be manipulated and/or contoured for disposal with one or more components of surgical system 10 and/or the structural anatomy of vertebrae, pre-operatively, in-situ and/or intra-operatively.

In some embodiments, body 14 is fabricated from a polymer mesh. In some embodiments, body 14 includes an agent, for example, allograft bone within a polymer mesh bag, covering and/or pouch to provide targeted and contained delivery of the allograft bone to selected tissue, as described herein. In some embodiments, the polymer mesh is configured to allow ingrowth of cells while also retaining bone graft within one or more cavities of body 14. In some embodiments, the polymer mesh allows natural cellular healing and remodeling mechanisms of the body to coordinate remodeling of bone by osteoclast cells and formation of new bone by osteoblast cells. In some embodiments, the polymer mesh is fabricated from a biodegradable suture material and provides effective cellular in-growth and complete resorption. In some embodiments, the polymer mesh is fabricated from natural materials, synthetic polymeric resorbable materials, synthetic polymeric non-resorbable materials, and other materials. In some embodiments, natural mesh materials include silk, extracellular matrix (such as DBM, collagen, ligament, tendon tissue, or other), silk-elastin, elastin, collagen, and cellulose. In some embodiments, synthetic polymeric resorbable materials include poly(lactic acid) (PLA), poly(glycolic acid) (PGA), poly (lactic acid-glycolic acid) (PLGA), polydioxanone, PVA, polyurethanes, polycarbonates, and others.

Body 14 includes an inner surface 20 that defines a cavity, such as, for example, a chamber 22 disposed between ends 16, 18. Chamber 22 is configured for disposal of an agent, as described herein. In some embodiments, surface 20 may have various surface configurations, such as, for example, rough, arcuate, undulating, porous, semi-porous, dimpled, polished and/or textured. In some embodiments, surface 20 defines one or a plurality of cavities, which may be distinct and separate, or configured to communicate, for example, via connecting openings that facilitate the flow of gas or fluid between the cavities.

Body 14 includes a layer 32 and a layer 34. Layers 32, 34 extend between ends 16, 18. Layer 32 is connectable with layer 34 to form receptacle body 14. Layer 32 is connectable with layer 34 to form a perimeter P of body 14, as shown in FIG. 1. In some embodiments, layers 32, 34 are connected pre-operatively, in-situ and/or intra-operatively to dispose body 14 in a selected implant configuration. In some embodiments, one or more portions of layer 32 can be connected with one or more portions of layer 34, for example, by a heat seal, adhesion, pressure fittings, coil ring, draw string, stitches, sutures, twist tie or combinations thereof, to form body 14 and/or one or more chambers 22, as described herein.

Layer 32 is engaged with layer 34 to form a connecting wall, such as, for example, a boundary 36 disposed about chamber 22. Layers 32, 34 are connected to form a selected configuration of the receptacle of spinal implant 12 and/or one or more chambers 22 of body 14. Layer 32 includes a surface 40 and layer 34 includes a surface 42. Surfaces 40, 42 are disposed for engagement to form a seam 44. In some embodiments, seam 44 is formed, for example, by a heat seal, adhesion, pressure fittings, coil ring, draw string, stitches, sutures, twist tie or combinations thereof.

In some embodiments, seam 44 forms a seal about chamber 22 to resist and/or prevent passage and/or expulsion of an agent, as described herein, from chamber 22. In some embodiments, seam 44 forms a gas and/or fluid tight seal about chamber 22 that prevents passage and/or expulsion of an agent from chamber 22. In some embodiments, seam 44 forms a seal about chamber 22 that selectively allows the passage and/or expulsion of an agent from chamber 22, for example, via one or more selectively positioned and/or spaced apart openings disposed along seam 44. In some embodiments, body 14 can include one or more boundaries to form one or more cavities of the spinal implant receptacle. In some embodiments, body 14 can include one or more equally sized chambers, as described herein. In some embodiments, body 14 can include one or more alternately sized chambers, as described herein.

Layers 32, 34 are engageable to form seam 44 and a selected configuration of chamber 22. Chamber 22 includes an overall rectangular configuration and a substantially rectangular cross-section with arcuate edges to seam 44. In some embodiments, chamber 22 may have alternate configurations, such as, for example, oval, cylindrical, triangular, square, polygonal, irregular, uniform, non-uniform, offset, staggered, undulating, arcuate, variable and/or tapered.

Wall 30 includes a surface 50 that defines openings 52. Openings 52 extend through layers 32, 34 and provide an aperture for disposal of a surgical instrument and/or a bone fastener to facilitate positioning of spinal implant 12 with tissue. Openings 52 are configured for disposal of a surgical instrument and/or a bone fastener to align and/or guide spinal implant 12 into engagement with tissue, such as, for example, vertebrae.

In some embodiments, a surgical instrument and/or a bone fastener can be disposed with one or more openings 52 to allow for accurate and secure placement of the spinal implant receptacle in a lateral gutter of laminae. In some embodiments, surface 50 can be disposed about a head of a bone fastener and/or laminar fusions. As such, spinal implant 12 can be placed using bone fastener trajectories, and the bone fastener heads. For example, as the bone fasteners are tightened through one or more openings 52, the bone fasteners tighten or clamp body 14 for attachment with tissue and maintain spinal implant 12 in place for fusion. In some embodiments, surface 50 can be disposed about one or more guidewires such that spinal implant 12 can be pulled through tissue with an inserter and the retaining geometry of body 14 disposed around the guidewire.

In some embodiments, the agent, as described herein, may be disposed, packed, coated or layered within, on, adjacent or about the components and/or surfaces of surgical system 10, and/or disposed with tissue. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration. In some embodiments, the bone graft may include bone material including autograft, allograft, xenograft, MASTERGRAFT®, collagen or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, TCP, HA-TCP, calcium sulfate, or other resorbable polymers such as polylactide, polyglycolide, polytyrosine carbonate, polycaprolactone and their combinations. In some embodiments, the bone graft comprises demineralized bone material, which may include demineralized bone, powder, chips, triangular prisms, spheres, cubes, cylinders, shards, fibers or other shapes having irregular or random geometries. In some embodiments, the bone graft comprises at least one growth factor. These growth factors include osteoinductive agents, for example, agents that cause new bone growth in an area where there was none and/or osteoconductive agents, for example, agents that cause in growth of cells into and/or through the allograft. Osteoinductive agents can be polypeptides or polynucleotides compositions.

In assembly, operation and use, surgical system 10, similar to the systems and methods described herein, is employed to treat a selected section of vertebrae V, as shown in FIGS. 3-6. A medical practitioner obtains access to a surgical site including vertebrae V in any appropriate manner, such as through incision and retraction of tissues. In some embodiments, surgical system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating a spine disorder. In some embodiments, one or all of the components of surgical system 10 can be delivered or implanted as a pre-assembled device, intra-operatively or can be assembled in situ. The components of surgical system 10 may be completely or partially revised, removed or replaced.

In some embodiments, a surgical procedure includes a posterolateral gutter fusion surgery such that an incision is made in a body of a patient and one or more screw trajectories T are identified via medical imaging, such as, for example, a C-Arm. A pedicle access kit (PAK) needle (not shown) is utilized to provide access to vertebral tissue including laminae, transverse processes, pedicles and/or adjacent tissue. In one example, the PAK needle is placed at an intersection of a facet and a transverse process. The PAK needle is advanced across a junction of the pedicle and a selected vertebral body. An inner stylet of the PAK needle is removed to allow a guidewire 202 to be inserted. The PAK needle is removed. A fusion bed of tissue, for example, adjacent lumbar vertebral levels L4, L5 is decorticated along a lateral gutter of L4, L5.

Spinal implant 12 is selected for disposal with the structural anatomy of tissue including the prepared fusion bed along the lateral gutter of L4, L5 and adjacent tissue. The selected configuration and/or features of spinal implant 12 can include selection of one or more agents, as described herein, and/or selection of the configuration of body 14, as described herein, for accurate and secure placement of the components of spinal implant 12 with the prepared fusion bed along the lateral gutter of L4, L5, and/or around bone fasteners 200 during surgical treatment. In some embodiments, the selected configuration of body 14 can include selected parameters, such as, for example, geometry, porosity, material, mesh type and/or chamber 22 configuration, as described herein. In some embodiments, spinal implant 12 and/or one or more components of spinal implant 12 can be connected and/or assembled pre-operatively, in-situ and/or intra-operatively. In some embodiments, spinal implant 12 and/or one or more components of spinal implant 12 can be connected and/or assembled on a back table of an operating room, pre-operatively or intra-operatively. In some embodiments, surgical system 10 comprises a kit including one or a plurality of alternately configured spinal implants 12 and/or one or more components of spinal implant 12 for connection and/or assembly. In some embodiments, surgical system 10 comprises a kit including a series of spinal implants 12 comprising bags with varying geometries, features and mesh types that contain one or more agents, as described herein. In some embodiments, the kit includes one or a plurality of single use, agent fillable bags of alternate configuration.

Figure 3:
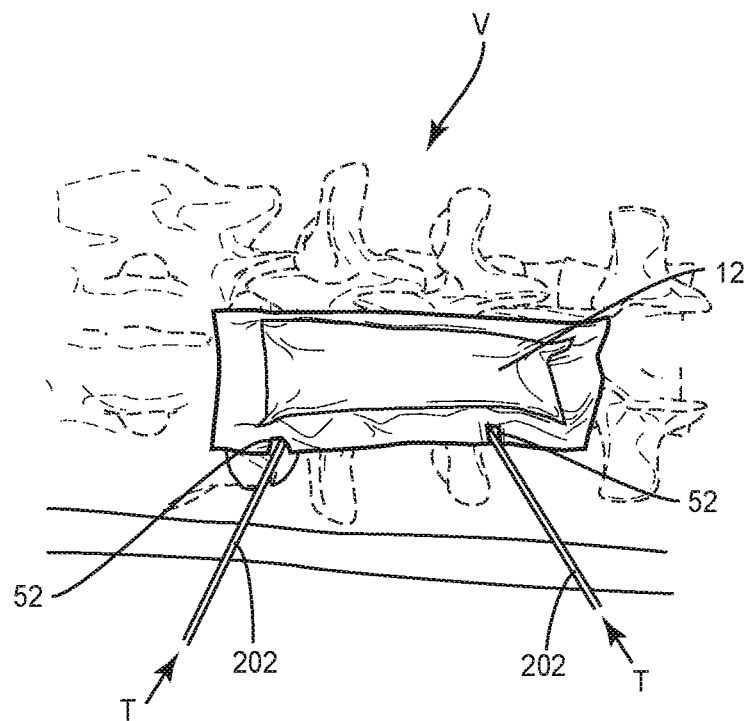
FIG. 3 is a plan view of components of one embodiment of a surgical system in accordance with the principles of the present disclosure disposed with vertebrae.

The configuration and/or features of spinal implant 12, as shown in FIG. 3, are selected, as described herein, for disposal with the prepared fusion bed along the lateral gutter of L4, L5, and/or around bone fasteners 200 in connection with the posterolateral gutter fusion surgery. In some embodiments, one or more agents are disposed with surface 20 and layers 32, 34 are engaged intra-operatively to form seam 44 to define chamber 22 for containment of the one or more agents.

Figure 4:
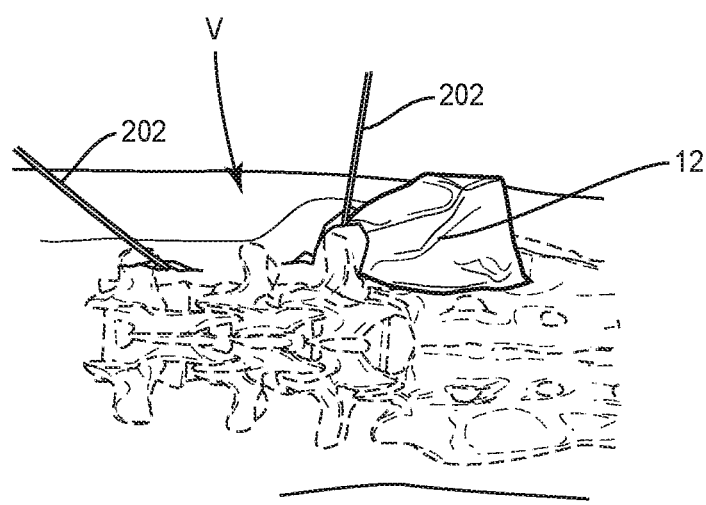
FIG. 4 is a plan view of components of one embodiment of a surgical system in accordance with the principles of the present disclosure disposed with vertebrae.
Figure 5:
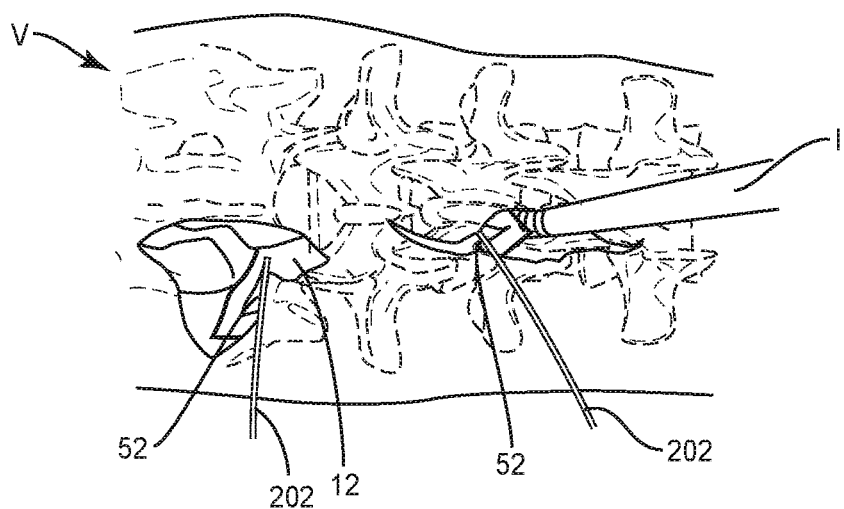
FIG. 5 is a plan view of components of one embodiment of a surgical system in accordance with the principles of the present disclosure disposed with vertebrae.
Figure 6:
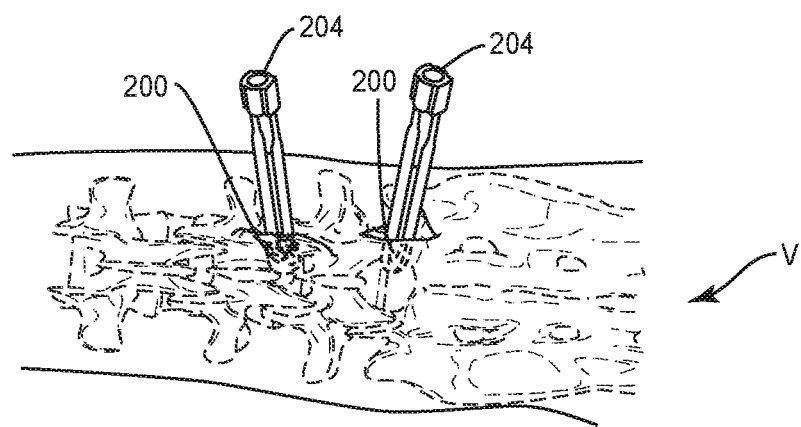
FIG. 6 is a plan view of components of one embodiment of a surgical system in accordance with the principles of the present disclosure disposed with vertebrae.
Figure 7:
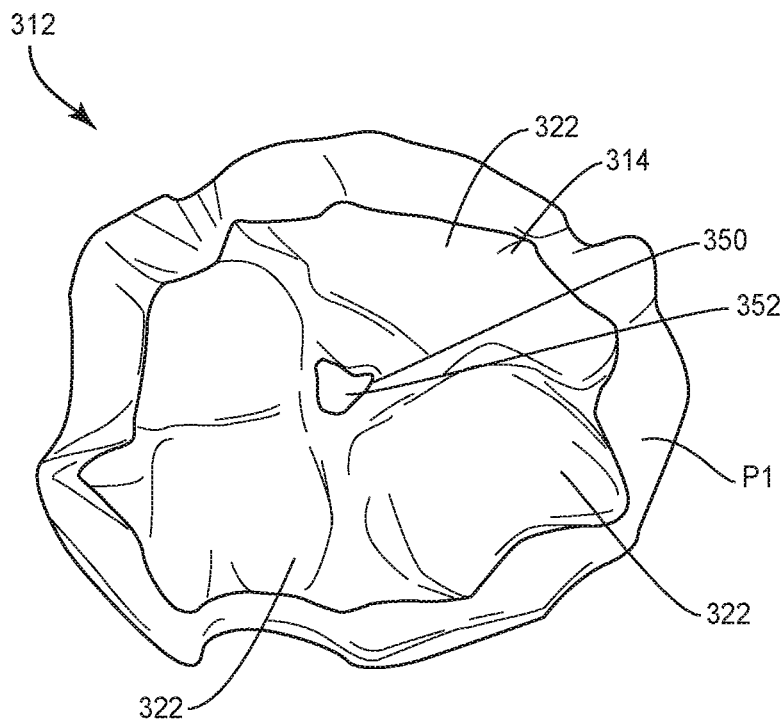
FIG. 7 is a perspective view of components of one embodiment of a surgical system in accordance with the principles of the present disclosure.
Figure 8:
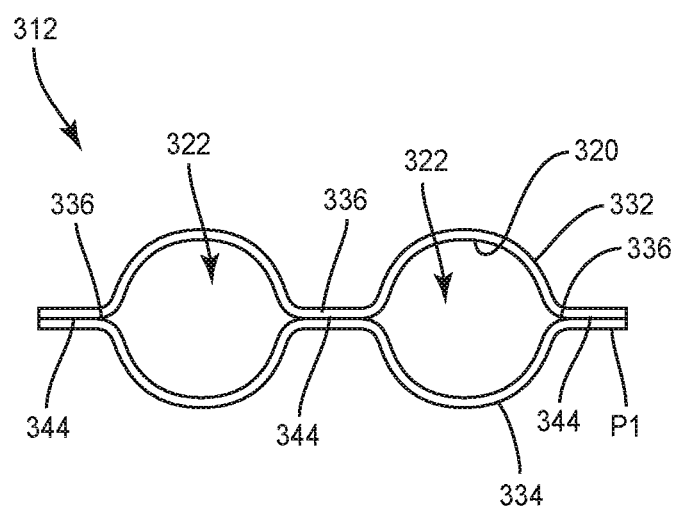
FIG. 8 is a cross section view of the components of the system shown in FIG. 7.

Spinal implant 12 is introduced through the incision, as shown in FIG. 4, for delivery adjacent to the prepared fusion bed along the lateral gutter of L4, L5. Spinal implant 12 is connected with an inserter I, as shown in FIG. 5, and drawn through the incision to position body 14 with the lateral gutter and orient openings 52 for disposal about guidewires 202. Guidewires 202 are disposed within openings 52 such that bone fasteners 200 can be aligned with openings 52. Inserter I is disengaged from body 14. Extenders 204 with bone fasteners 200 removably attached thereto are delivered along guidewires 202 to the surgical site including the lateral gutter. Bone fasteners 200 are aligned with openings 52 for disposal therein. Bone fasteners 200 are engaged with tissue adjacent the L4, L5 vertebrae and guidewires 202 are removed from the tissue, as shown in FIG. 6. Bone fasteners 200 are disposed within openings 52. As bone fasteners 200 are tightened with tissue through openings 52, bone fasteners 200 tighten or clamp body 14 for attachment with the prepared fusion bed along the lateral gutter of L4, L5 and maintain spinal implant 12 in place for fusion. In some embodiments, a spinal rod (not shown) may be connected with bone fasteners 200.

In some embodiments, surgical system 10 may be employed with spinal rods, connectors, plates, bone fasteners and/or fixation elements along a single vertebral level or a plurality of vertebral levels. Upon completion of the procedure, the surgical instruments, assemblies and non-implanted components of surgical system 10 are removed and the incisions are closed. The components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In some embodiments, the components of surgical system 10 contain radiomarkers and/or radioopacity enhancing agents. In some embodiments, the radiomarkers and/or radioopacity enhancing agents enable the surgeon the ability to visualize, for example, via C-arm radiography, the delivery of the components of spinal implant 12 to the site and assess the quality of implant at the intended delivery site. In some embodiments, the radiomarkers include, but are not limited to, barium, calcium phosphate, bismuth, iodine, tantalum, tungsten, and/or metal beads or particles.

In some embodiments, surgical system 10 may comprise various surgical instruments, such as, for example, drivers, inserters, extenders, reducers, spreaders, distractors, reamers, decorticating devices, blades, forceps, elevators and drills, which may be alternately sized and dimensioned, and arranged as a kit. In some embodiments, surgical system 10 may comprise the use of microsurgical and image guided technologies, such as, for example, surgical navigation components employing emitters and sensors, which may be employed to track introduction and/or delivery of the components of surgical system 10 and the surgical instruments described to a surgical site. See, for example, the surgical navigation components and their use as described in U.S. Pat. Nos. 6,021,343, 6,725,080, 6,796,988, the entire contents of each of these references being incorporated by reference herein.

In one embodiment, as shown in FIGS. 7-10, surgical system 10, similar to the systems and methods described above with regard to FIGS. 1-6, includes a spinal implant 312, similar to spinal implant 12 described herein. Spinal implant 312 includes a receptacle configured for disposal of one or more agents, as described herein, and a body 314, similar to body 14 described herein. Body 314 comprises an overall circular configuration and a cross-section of separate cavities, as described herein, with edges extending to a connecting wall, similar to that described herein.

Body 314 includes an inner surface 320 that defines a plurality of cavities, such as, for example, chambers 322, similar to chamber 22 described herein. Chambers 322 are configured for disposal of an agent, as described herein. Body 314 includes a layer 332 and a layer 334, which are connectable to form receptacle body 314. Layer 332 is connectable with layer 334 to form a perimeter P1 of body 314. In some embodiments, layers 332, 334 are connected pre-operatively, in-situ and/or intra-operatively to dispose body 314 in a selected implant configuration, similar to that described herein.

Layer 332 is engaged with layer 334 to form a connecting wall, such as, for example, a boundary 336 disposed about chambers 322. Layers 332, 334 are connected to form a selected configuration of the receptacle of spinal implant 312 and chambers 322 of body 314. Layers 332, 334 include surfaces disposed for engagement to form a seam 344, similar to seam 44 described herein, about chambers 322. Layers 332, 334 are engageable to form seam 344 and a selected configuration of chambers 322. Chambers 322 are separate and spaced apart in a circumferential orientation about body 314. Each chamber 322 has a substantially circular cross-section with edges to seam 344. In some embodiments, one or more of chambers 322 may include a spherical configuration.

Wall 330 includes a surface 350 that defines an opening 352, similar to opening 52 described herein. Opening 352 extends through layers 332, 334 and provides an aperture for disposal of a surgical instrument and/or a bone fastener to facilitate positioning of spinal implant 312 with tissue. Opening 352 is configured for disposal of a surgical instrument and/or a bone fastener to align and/or guide spinal implant 312 into engagement with tissue, such as, for example, vertebrae.

Figure 9:
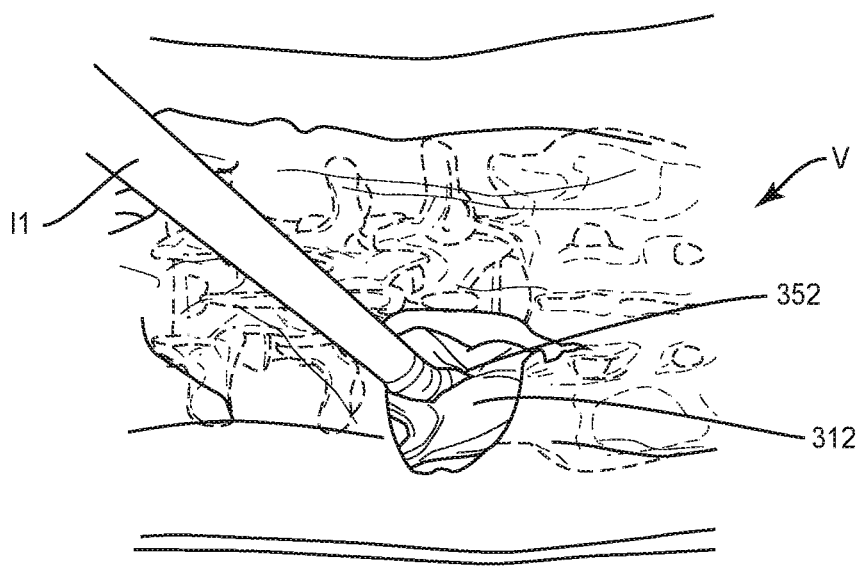
FIG. 9 is a plan view of components of one embodiment of a surgical system in accordance with the principles of the present disclosure disposed with vertebrae.
Figure 10:
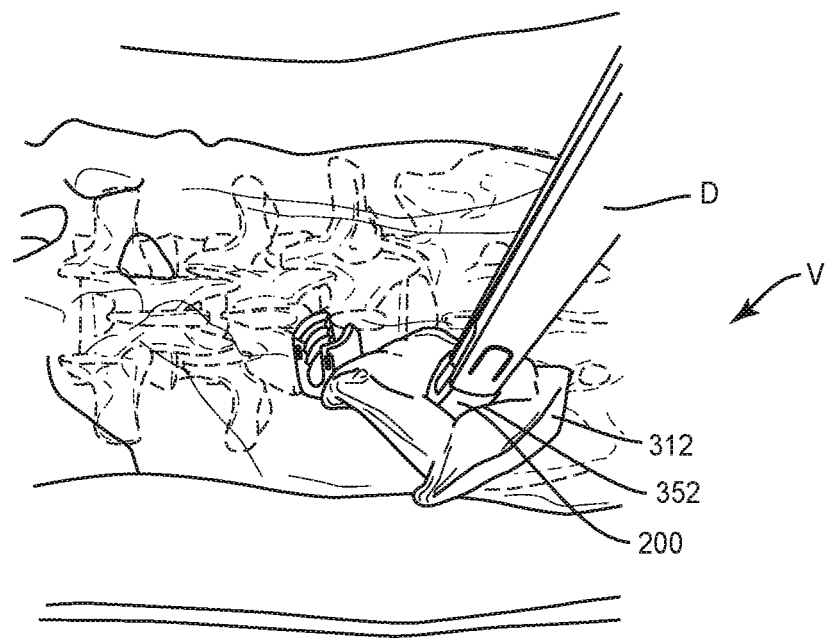
FIG. 10 is a plan view of components of one embodiment of a surgical system in accordance with the principles of the present disclosure disposed with vertebrae.

In assembly, operation and use, surgical system 10 is employed with spinal implant 312, similar to the systems and methods described with regard to FIGS. 1-6, to treat a selected section of vertebrae V, as shown in FIGS. 9 and 10. A medical practitioner obtains access to a surgical site including vertebrae V in connection with a posterolateral gutter fusion surgery, similar to that described herein. An incision is made in a body of a patient to provide access to vertebral tissue including laminae, transverse processes, pedicles and/or adjacent tissue. A surgical navigation enabled drill (not shown) decorticates a fusion bed adjacent lumbar vertebral levels L4, L5 along a lateral gutter of L4, L5. The surgical navigation drill includes a navigation component connected therewith to facilitate communication with one or more sensors of a surgical navigation system during the surgical procedure. See, for example, the surgical navigation components and their use as described in U.S. Pat. Nos. 6,021,343, 6,725,080, 6,796,988. The navigation component generates a signal representative of a position of the surgical navigation drill relative to tissue.

Spinal implant 312 is selected, similar to that described herein, for disposal with the structural anatomy of tissue including the prepared fusion bed along the lateral gutter of L4, L5 and adjacent tissue and/or around a bone fastener 200, disposable with opening 352, in connection with the posterolateral gutter fusion surgery. In some embodiments, one or more agents are disposed with surface 320 and layers 332, 334 are engaged intra-operatively to form seam 344 to define chambers 322 for containment of the one or more agents.

Spinal implant 312 is introduced through the incision, as shown in FIG. 9, for delivery adjacent to the prepared fusion bed along the lateral gutter of L4, L5. Spinal implant 312 is connected with a surgical navigation enabled inserter 11, similar to the surgical navigation enabled instruments described herein, and introduced through the incision to position body 314 with the lateral gutter. Inserter 11 is disengaged from body 314. A surgical navigation enabled driver D, similar to the surgical navigation enabled instruments described herein, is connected with a bone fastener 200 for delivery to the surgical site including the lateral gutter. Bone fastener 200 is aligned with opening 352 for disposal therein. Bone fastener 200 is engaged with tissue adjacent the L4, L5 vertebrae, as shown in FIG. 10. Bone fastener 200 is disposed within opening 352. As bone fastener 200 is tightened with tissue through opening 352, bone fasteners 200 tightens or clamps body 314 for attachment with the prepared fusion bed along the lateral gutter of L4, L5 and maintains spinal implant 312 in place for fusion. Upon completion of the procedure, the surgical instruments, assemblies and non-implanted components of surgical system 10 are removed and the incision is closed.

Figure 11:
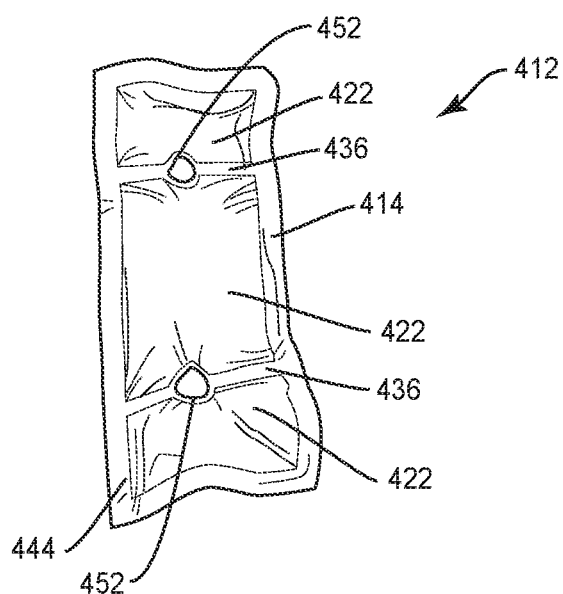
FIG. 11 is a plan view of components of one embodiment of a surgical system in accordance with the principles of the present disclosure.
Figure 12:
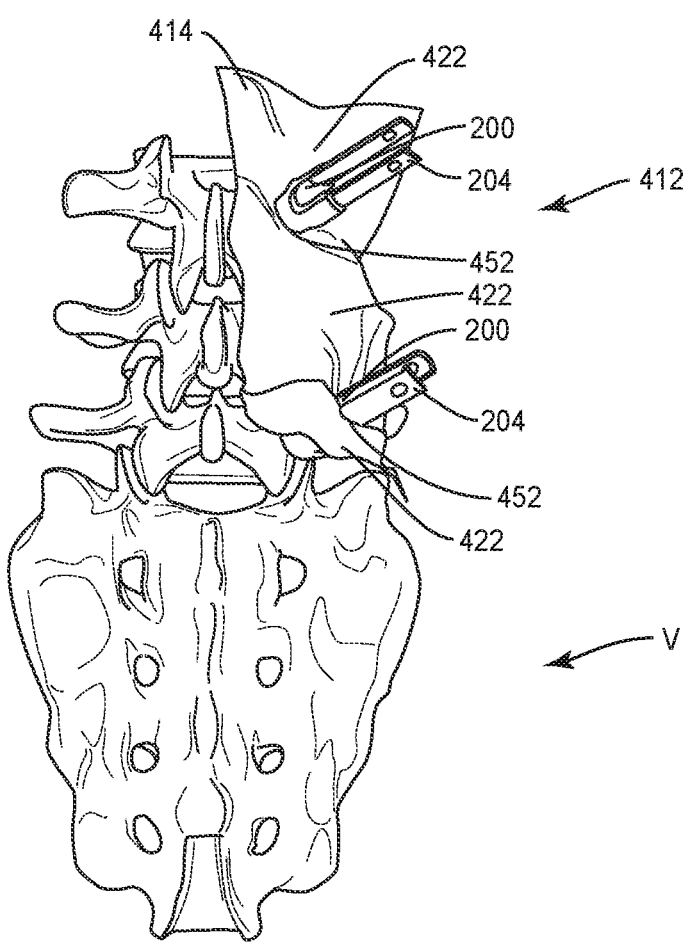
FIG. 12 is a plan view of components of one embodiment of a surgical system in accordance with the principles of the present disclosure disposed with vertebrae.

In one embodiment, as shown in FIGS. 11 and 12, surgical system 10, similar to the systems and methods described herein, includes a spinal implant 412, similar to spinal implant 12 described herein. Spinal implant 412 includes a receptacle configured for disposal of one or more agents, as described herein, and a body 414, similar to body 14 described herein. Body 414 comprises an overall rectangular configuration and a cross-section of separate cavities, as described herein, with edges extending to a connecting wall, similar to that described herein.

Body 414 defines a plurality of chambers 422, similar to chamber 22 described herein. Chambers 422 are configured for disposal of an agent, as described herein. Body 414 includes layers, similar to that described herein, which are connectable to form receptacle body 414 and a boundary 436 disposed about chambers 422. The layers of body 414 are connected to form a selected configuration of the receptacle of spinal implant 412 and chambers 422. The layers of body 414 include surfaces disposed for engagement to form a seam 444, similar to seam 44 described herein, about chambers 422. Chambers 422 are separate and spaced apart in a serial and/or linear orientation along body 414.

Boundary 436 defines openings 452, similar to opening 52 described herein. Openings 452 provide an aperture for disposal of a surgical instrument and/or a bone fastener to facilitate positioning of spinal implant 412 with tissue. Openings 452 are configured for disposal of a surgical instrument and/or a bone fastener to align and/or guide spinal implant 412 into engagement with tissue, such as, for example, vertebrae.

In assembly, operation and use, surgical system 10 is employed with spinal implant 412, similar to the systems and methods described herein, to treat a selected section of vertebrae V, as shown in FIG. 12. A medical practitioner obtains access to a surgical site including vertebrae V in connection with a posterolateral gutter fusion surgery to prepare a fusion bed adjacent lumbar vertebral levels along a lateral gutter, similar to that described herein.

Spinal implant 412 is selected, similar to that described herein, for disposal with the structural anatomy of tissue including the prepared fusion bed. Spinal implant 412 is introduced through an incision and connected with an inserter, similar to that described herein, for delivery adjacent to the prepared fusion bed. Extenders 204 with bone fasteners 200 removably attached thereto are delivered to the surgical site including the lateral gutter. Bone fasteners 200 are aligned with openings 452 for disposal therein. Bone fasteners 200 are engaged with tissue adjacent the vertebrae, as shown in FIG. 12. Bone fasteners 200 are disposed within openings 452. As bone fasteners 200 are tightened with tissue through openings 452, bone fasteners 200 tighten or clamp body 414 for attachment with the prepared fusion bed and maintain spinal implant 412 in place for fusion. Upon completion of the procedure, the surgical instruments, assemblies and non-implanted components of surgical system 10 are removed and the incision is closed.

Figure 13:
FIG. 13 is a plan view of components of one embodiment of a surgical system in accordance with the principles of the present disclosure.
Figure 14:
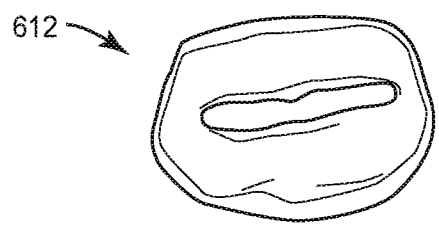
FIG. 14 is a plan view of components of one embodiment of a surgical system in accordance with the principles of the present disclosure.
Figure 15:
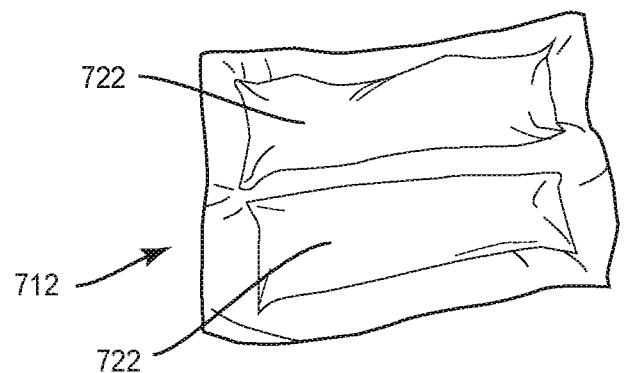
FIG. 15 is a plan view of components of one embodiment of a surgical system in accordance with the principles of the present disclosure.

In some embodiments, surgical system 10 comprises a kit including one or a plurality of alternately configured spinal implants and/or one or more components of a spinal implant for connection and/or assembly. In some embodiments, the kit includes a spinal implant 512 having a square configuration, as shown in FIG. 13. In some embodiments, the kit includes a spinal implant 612 having an oval configuration, as shown in FIG. 14, and a centrally disposed elongated slot, similar to the openings described herein. In some embodiments, the kit includes a spinal implant 712, as shown in FIG. 15, having dual elongated chambers 722, similar to the chambers described herein, which are spaced apart and disposed in side by side and/or parallel orientation.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a body including proximal and distal layers, the distal layer being engaged with the proximal layer to form a connecting wall, inner surfaces of the layers defining a plurality of spaced apart cavities, the connecting wall being disposed about the cavities, the body including an opening extending through the proximal and distal layers, the opening being spaced apart from the cavities such that the opening is not in communication with the cavities and the cavities surround the opening, the layers being connected intra-operatively, the connecting wall including a seam that creates a seal disposed about the cavities; and
an agent disposable with the cavities, the agent comprising autograft or allograft.

2. A spinal implant as recited in claim 1, wherein the layers are connected intra-operatively to dispose the body in a selected implant configuration.

3. A spinal implant as recited in claim 1, wherein the connecting wall includes a perimeter of the body disposed about the cavities.

4. A spinal implant as recited in claim 1, wherein the opening includes an elongated slot centrally disposed with the body.

5. A spinal implant as recited in claim 1, wherein the cavities define a plurality of equally sized chambers.

6. A spinal implant as recited in claim 1, wherein the cavities define a plurality of alternately sized chambers.

7. A spinal implant as recited in claim 1, wherein the body comprises a porous mesh.

8. A spinal implant as recited in claim 1, wherein the body comprises an overall circular configuration.

9. A spinal implant as recited in claim 1, wherein the body is fabricated from an elastic material.

10. A spinal implant as recited in claim 1, further comprising a bone fastener disposed in the opening and first and second extenders, the extenders each being removably coupled to the bone fastener.

11. A spinal implant as recited in claim 10, wherein the bone fastener includes a head having spaced apart arms that define an implant cavity therebetween configured for disposal of a spinal rod.

12. A spinal implant as recited in claim 1, wherein the cavities are spaced apart from the opening by the seal.

13. A spinal implant as recited in claim 1, wherein the seal is configured to allow passage of the agent from at least one of the cavities.

14. A spinal implant system comprising:
a polymer mesh body including proximal and distal layers, inner surfaces of the layers defining a plurality of spaced apart cavities, the body further including a boundary disposed about the cavities, the body including an opening extending through the layers, the opening being spaced apart from the cavities such that the opening is not in communication with the cavities and the cavities surround the opening, the distal layer being connected intra-operatively to the proximal layer, a seal being disposed about the opening;
at least one bone fastener disposable with the opening; and
an agent disposable with the cavities,
wherein the seal is configured to allow passage of the agent from at least one of the cavities.

15. A spinal implant system as recited in claim 14, wherein the agent comprises an osteoinductive agent or an osteoconductive agent.

16. A spinal implant system as recited in claim 14, wherein the polymer mesh body is configured to allow ingrowth of cells while also retaining the agent within the cavities.

* * * * *